US012478109B2

(12) United States Patent
Lauenstein et al.

(10) Patent No.: US 12,478,109 B2
(45) Date of Patent: Nov. 25, 2025

(54) MEMS SOUND GENERATION FOR AEROSOL-GENERATING DEVICES AND RELATED USER INTERFACES AND METHODS

(71) Applicant: PHILIP MORRIS PRODUCTS S.A., Neuchâtel (CH)

(72) Inventors: Stefan Lauenstein, Neuchâtel (CH); Michel Bessant, Neuchâtel (CH)

(73) Assignee: Philip Morris Products S.A., Neuchâtel (CH)

(*) Notice: Subject to any disclaimer, the term of this patent is extended or adjusted under 35 U.S.C. 154(b) by 589 days.

(21) Appl. No.: 16/644,790

(22) PCT Filed: Sep. 4, 2018

(86) PCT No.: PCT/IB2018/056750
§ 371 (c)(1),
(2) Date: Mar. 5, 2020

(87) PCT Pub. No.: WO2019/049028
PCT Pub. Date: Mar. 14, 2019

(65) Prior Publication Data

US 2021/0059313 A1 Mar. 4, 2021

(30) Foreign Application Priority Data

Sep. 7, 2017 (EP) .................................... 17189834

(51) Int. Cl.
*A24F 40/50* (2020.01)
*A24F 40/20* (2020.01)
(Continued)

(52) U.S. Cl.
CPC .............. *A24F 40/50* (2020.01); *A24F 40/20* (2020.01); *A24F 40/53* (2020.01); *A24F 40/60* (2020.01);
(Continued)

(58) Field of Classification Search
None
See application file for complete search history.

(56) References Cited

U.S. PATENT DOCUMENTS

2010/0163063 A1* 7/2010 Fernando ................ A24F 40/85 131/184.1
2011/0226242 A1* 9/2011 Von Hollen ...... A61M 15/0023 128/203.12
(Continued)

FOREIGN PATENT DOCUMENTS

CN 202445136 U 9/2012
CN 104053100 A 9/2014
(Continued)

OTHER PUBLICATIONS

Klasco, MEMS Microspeakers are Truly Digital Transducers, Aug. 27, 2015, Audio Express (republished from Voic Coil May 2015). (Year: 2015).*
(Continued)

*Primary Examiner* — Anthony Calandra
(74) *Attorney, Agent, or Firm* — Mueting Raasch Group

(57) ABSTRACT

A MEMS sound generator may be used to produce high-fidelity sound for an aerosol-generating device. The MEMS sound generator may compress air to produce sound using a plurality of drivers at a plurality of frequencies. The sound may emulate the sound of one or more conventional uses of smoking materials, emulate a masking noise, or include information. The sound generated may be modulated based on a user's puff. A user interface may be provided to configure the aerosol-generating device.

20 Claims, 6 Drawing Sheets

Figure 1:
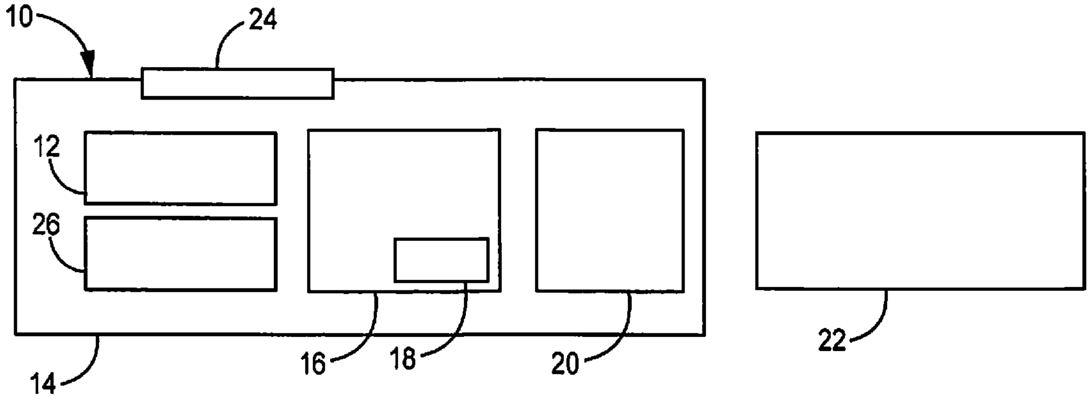

(51) Int. Cl.

| | |
|---|---|
| ***A24F 40/53*** | (2020.01) |
| ***A24F 40/60*** | (2020.01) |
| ***A61M 15/06*** | (2006.01) |
| ***H04R 1/00*** | (2006.01) |
| *A24F 40/10* | (2020.01) |

(52) U.S. Cl.

CPC ............... *A61M 15/06* (2013.01); *H04R 1/00* (2013.01); *A24F 40/10* (2020.01); *H04R 2201/003* (2013.01)

(56) References Cited

U.S. PATENT DOCUMENTS

| | | | | |
|---|---|---|---|---|
| 2014/0246035 | A1 | 9/2014 | Minskoff et al. | |
| 2014/0270271 | A1 | 9/2014 | Dehe et al. | |
| 2015/0013693 | A1* | 1/2015 | Fuisz | A24C 5/60 131/290 |
| 2015/0181930 | A1 | 7/2015 | Liu | |
| 2015/0238713 | A1 | 8/2015 | Cohen et al. | |
| 2015/0245659 | A1* | 9/2015 | DePiano | F22B 1/282 392/397 |
| 2015/0257445 | A1 | 9/2015 | Henry, Jr. et al. | |
| 2016/0128389 | A1 | 5/2016 | Lamb et al. | |
| 2016/0136063 | A1* | 5/2016 | Niimi | A61K 8/365 424/63 |
| 2016/0219933 | A1 | 8/2016 | Henry, Jr. et al. | |
| 2016/0337362 | A1 | 11/2016 | Cameron | |
| 2016/0338407 | A1* | 11/2016 | Kerdemelidis | A24F 40/60 |
| 2016/0360320 | A1 | 12/2016 | Margalit | |
| 2017/0020196 | A1 | 1/2017 | Cameron | |
| 2017/0020197 | A1* | 1/2017 | Cameron | G08B 5/36 |
| 2017/0318861 | A1* | 11/2017 | Thorens | A24F 40/53 |
| 2018/0146708 | A1* | 5/2018 | Batista | A24F 40/485 |
| 2019/0053538 | A1* | 2/2019 | Batista | G06K 19/0723 |

FOREIGN PATENT DOCUMENTS

| | | | |
|---|---|---|---|
| CN | 204070537 | U | 1/2015 |
| CN | 105167201 | A | 12/2015 |
| CN | 106455716 | A | 2/2017 |
| EP | 3075266 | A1 | 10/2016 |
| EP | 2849589 | B1 | 7/2017 |
| JP | 2009-538553 | A | 11/2009 |
| KR | 2002-0067473 | A | 8/2002 |
| RU | 2517125 | | 5/2014 |
| WO | WO 2007/135679 | A2 | 11/2007 |
| WO | 2010073122 | | 7/2010 |
| WO | WO 2015/109618 | A1 | 7/2015 |
| WO | WO 2016/023809 | A1 | 8/2015 |

OTHER PUBLICATIONS

Headphonesty, Understanding Sample Rate, Bit Depth, and Bit Rate (downloaded online Aug. 13, 2022), 2021. (Year: 2021).*

Partial European Search Report for 17189834.9, issued by the European Patent Office on Mar. 13, 2018; 14 pgs.

International Search Report and Written Opinion issued by the European Patent Office for PCT/IB2018/056750, 19 pgs.

International Preliminary Report on Patentability, issued by the European Patent Office for PCT/IB2018/056750, 21 pgs.

Russian Office Action for RU 2020112289 issued by the Russian Patent Office, Feb. 10, 2022; 11 pgs. including English translation.

Japanese Office Action for JP 2020-512038, issued by the Japanese Patent Office on Oct. 17, 2022; 9 pgs. including English translation.

Chinese Office Action for CN 201880052752.9 issued by the China National Intellectual property Administration on Oct. 14, 2022; 29 pgs. including English translation.

* cited by examiner

MEMS SOUND GENERATION FOR AEROSOL-GENERATING DEVICES AND RELATED USER INTERFACES AND METHODS

This application is the § 371 U.S. National Stage of International Application No. PCT/IB2018/056750, filed 4 Sep. 2018, which claims the benefit of European Application No. 17189834.9, filed 7 Sep. 2017, the disclosures of which are incorporated by reference herein in their entireties.

This disclosure relates to sound generation. In particular, this disclosure relates to MEMS sound generation for an aerosol-generating device and related user interfaces and methods.

Handheld aerosol-generating devices, such as cartomizer electronic cigarettes, are known, which utilize liquid to be evaporated or tobacco material to be heated to generate an inhalable aerosol. These devices may provide an alternative experience to conventional combustion cigarettes. Some devices may adopt a similar look and feel to conventional cigarettes, which may be familiar, easy to handle, portable, and easy to manufacture. Some devices have an internal breath-activated switch or button switch to activate the generation, or release, of the inhalable aerosol.

Whereas some smoking materials have characteristic sounds during use, many electronic cigarettes do not produce sound. Some electronic cigarettes that do produce sound do not adequately reproduce the experience of using smoking material in a convincing manner, particularly if the sound is complex and intricate, such as the sound of burning kretek in Indonesian cigarettes, which may be described as a "crackling" sound. This inadequate experience may be undesirable to users of such conventional cigarettes. Further, electronic cigarettes may inherently produce sounds during use that may be undesirable to users. Furthermore, electronic cigarettes often operate differently than conventional cigarettes and may have features that are unfamiliar to users.

It would be desirable to provide users with an improved experience with aerosol-generating devices that adequately emulates the sound of conventional uses of smoking material in a convincing manner. It would also be desirable to provide users with the option of mitigating undesirable sounds from aerosol-generating devices. It would further be desirable to help users understand how to use, configure, and maintain the aerosol-generating devices.

This disclosure provides a MEMS sound generator used to produce sound for an aerosol-generating device. The MEMS sound generator may compress air to produce sound. The MEMS sound generator may provide sound using a plurality of drivers to produce sound at a plurality of frequencies. The sound may be described as "high fidelity." The sound may emulate the sound of one or more conventional uses of smoking materials, emulate a masking noise, or include information. The sound generated may be modulated based on a user's puff. A user interface may be provided to configure the aerosol-generating device.

In one or more aspects, an aerosol-generating device may include an aerosolizer to generate aerosol from an aerosol-generating substrate. The aerosol-generating device may also include a MEMS sound generator. The aerosol-generating device may further include a controller operatively coupled to initiate the MEMS sound generator into producing sound.

In one or more aspects, a method for use with an aerosol-generating device may include detecting an action of a user using the aerosol-generating device. The method may also include producing sound using a MEMS sound generator in response to the action of the user.

In one or more aspects, the MEMS sound generator may compress air to produce the sound.

In one or more aspects, the MEMS sound generator may include a plurality of pressure-generating drivers arranged into an array to produce a plurality of different frequencies.

In one or more aspects, the sound may emulate the sound of a conventional use of a smoking material.

In one or more aspects, the sound may emulate the sound of burning kretek.

In one or more aspects, the sound may emulate a masking noise.

In one or more aspects, the sound may include information for a user.

In one or more aspects, an actuator may be operatively coupled to the controller, and the MEMS sound generator may produce the sound information in response to engagement of the actuator.

In one or more aspects, the information includes a voice message.

In one or more aspects, the information may provide an instruction to use or maintain the aerosol-generating device, a status of the aerosol-generating device, or both.

In one or more aspects, the MEMS sound generator may produce the sound in response to a user puff.

In one or more aspects, when the sound may be modulated, in one or more of intensity and frequency, in response to the user puff.

In one or more aspects, a puff sensor may be operatively coupled to the controller to measure the user puff.

In one or more aspects, the controller may be further configured to measure a characteristic of the aerosolizer to measure the user puff.

In one or more aspects, the aerosol-generating device may include the aerosol-generating substrate, and the substrate may include a nicotine material.

In one or more aspects, a user interface device may include a communication interface to communicate with the aerosol-generating device. The user interface device may also include a display having a user interface to present one or more graphical elements to configure the aerosol-generating device. The user interface device may further include a controller operably coupled to the display and communication interface. The controller may be configured to display the one or more graphical elements on the display. The controller may also be configured to allow a user selection using the one or more graphical elements via the user interface to configure the aerosol-generating device. The controller may further be configured to communicate with the aerosol-generating device using the communication interface to configure the aerosol-generating device based on the user selection.

In one or more aspects, the aerosol-generating device may be configured based on a configuration defining one or more of: a type of aerosol-generating substrate, a specific puff sound mode, a generic puff sound mode, an instruction mode, an error message mode, an operational message mode, a substrate detection mode, a substrate selection mode, a data download mode, a configuration mode, a volume level, and an audio quality level.

In one or more aspects, a non-transitory computer readable storage medium including a computer program stored which, when run on programmable electric circuitry, may cause the programmable electric circuitry to execute the method.

Utilizing the aerosol-generating device enables an immersive experience for the user that includes sound. Sound produced by the MEMS sound generator may be similar to, or even indistinguishable to an ordinary person from, the sound of conventional use of smoking material. For example, similar to a conventional use, when the user puffs harder (for example, draws air more quickly), a characteristic of the sound may also change. Sound produced may also mask undesirable sounds during operation of the aerosol-generating device. The user may also have access to instructions or status messages to facilitate ease of use of the aerosol-generating device.

The term "aerosol-generating device" refers to a device configured to couple to, or include, an aerosol generating substrate to generate aerosol. Preferably, the aerosol-generating device also includes an aerosolizer, such as an atomizer or heater.

The term "aerosol-generating substrate" refers to a device or substrate that releases, upon heating, volatile compounds that may form an aerosol to be inhaled by a user. Suitable aerosol-generating substrates may include plant-based material. For example, the aerosol-generating substrate may include tobacco or a tobacco-containing material containing volatile tobacco flavor compounds, which may be released from the aerosol-generating substrate upon heating. In addition, or alternatively, an aerosol-generating substrate may include a non-tobacco containing material. The aerosol-generating substrate may include homogenized plant-based material. The aerosol-generating substrate may include at least one aerosol former. The aerosol-generating substrate may include other additives and ingredients such as flavorants. Preferably, the aerosol-generating substrate is a liquid at room temperature. For example, the aerosol-generating substrate may be a liquid solution, suspension, dispersion or the like. In some preferred embodiments, the aerosol generating substrate includes glycerol, propylene glycol, water, nicotine and, optionally, one or more flavorants. Preferably, the aerosol-generating substrate includes nicotine material.

The term "tobacco" refers to a substance including tobacco, which includes tobacco blends or flavored tobacco, for example.

The term "kretek" refers to a blend of tobacco, cloves, and other optional flavors. When burned, the blend produces a characteristic crackling sound. Kretek may also refer to the crackling sound of burning cloves.

This disclosure relates to a microelectromechanical system (MEMS) sound generator for an aerosol-generating device. Although reference is made herein to aerosol-generating devices, such as electronic cigarettes, the MEMS sound generator may be used on any portable device. Various other applications will become apparent to one of skill in the art having the benefit of the present disclosure.

Any suitable MEMS sound generator can be used to produce sound. The sound generator may produce sound that covers at least the human audible range. The sound may cover at least a frequency range up to about 20 kHz, or at least between about 20 Hz and about 20 kHz. The sound may be formed of a plurality of frequencies. The decibel level capable of being produced at each of the frequencies may be sufficient to be heard by a user of the sound generator. The decibel levels may be adjustable.

The sound produced may be simple or high fidelity. An example of a simple sound may be the sound of a buzzer. Examples of high-fidelity sound include a crackling sound, a voice, or white noise. Preferably, the sound generator can produce high-fidelity sound.

The sound generator may produce sound by vibrating a membrane or compressing air to produce the sound. Preferably, the sound generator compresses air to produce sound.

The sound generator may include a plurality of pressure-generating drivers, which may also be described as micro-speakers. The pressure-generating drivers may be arranged into an array. The plurality of pressure-generating drivers may produce the plurality of frequencies. Each of the drivers may produce one or more of the plurality of frequencies. Preferably, each driver produces one of the frequencies. In some embodiments, the sound generator may use digital sound reconstruction (DSR). With DSR, the sound may be produced by the sound generator as a summation of discrete pulses produced from the array of pressure-generating drivers. Utilizing DSR may produce more accurate reproduction and less distortion than a conventional analog speaker, which varies the timing of the motion of a membrane.

The array may be disposed on one or more silicon chip or integrated circuit. Preferably, the drivers are disposed on a single silicon chip or integrated circuit. The sound generator may be described as an on-chip microspeaker array.

The sound generator may be a digital speaker. The sound generator may respond to digital signals. Digital sound data may be stored in memory and provided as one or more digital signals to the sound generator.

The sound generator may be small enough to fit into a body of an aerosol-generating device. The sound generator may fit into a volume less than or equal to about 10 mm×about 10 mm×about 10 mm. In some preferred embodiments, the sound generator may fit into a volume less than or equal to about 5 mm×about 5 mm×about 5 mm. In further preferred embodiments, the sound generator may fit into a volume of less than or equal to about 5 mm×about 5 mm×about 1.5 mm.

The sound produced by the sound generator may include a variety of sounds suitable for an aerosol-generating device. The sound may emulate another sound. The emulating sound may be produced in association with the aerosolizer being activated to generate aerosol. The sound production and aerosolization may be concurrent or at least overlapping in duration. Non-limiting examples of sounds to emulate include the sound of a conventional use of smoking material and a masking noise (for example, white noise). The sound may be initiated, produced, or triggered, in response to a user action, such as a user puff or engagement of an actuator.

When used with an aerosol-generating device, the sound generator may emulate the sound of a conventional use of a smoking material. The smoking material emulated may be kretek. The generated sound may emulate the sound of burning kretek.

The sound generator may produce or emulate a masking noise. The masking noise may be a "color" of noise, such as "white" noise. The aerosol-generating device may produce a sound, such as the sound when electronic cigarette liquid evaporates, which may be undesirable to the user or others around the user. By emulating a masking noise, such as white noise, the user or others nearby may perceive a cancellation of the undesirable sound.

White noise may be an equal, or substantially equal, intensity at all frequencies, at least in the human audible range. White noise may be emulated in practice by generating sound at random frequencies having an equal average intensity. Preferably, the audible sounds generated cover at least about 2 kHz to about 16 kHz or the entire human audible range.

In one or more embodiments, the aerosol-generating device may allow the user to select whether a specific puff sound or a generic puff sound is generated in response to a user puff.

Additionally, or alternatively, the sound may include information for a user. The sound information may be provided in the form of a voice message. Non-limiting examples of sound information provided include an instruction for the aerosol-generating device (for example, an audio tutorial or manual for using or maintaining the device) and a status of the aerosol-generating device. The status of the aerosol-generating device may include one or more of an error message, an indication of puffs left, an indication of a user interaction with the device (for example, actuator engaged), and an indication of a function of the device (for example, aerosolizer activated).

In one or more embodiments, the aerosol-generating device may allow the user to select whether a specific puff sound mode or information for the user is generated in response to a user action, such as a user puff.

In one or more embodiments, the aerosol-generating device may allow the user to generate a puff sound in response to a user puff and to generate information for the user in response to a different user action.

In one or more embodiments, the aerosol-generating device may allow the user to select whether a generic puff sound or information for a user is generated in response to a user action.

In one or more embodiments, the aerosol-generating device may allow the user to select whether a specific puff sound or voice message for a user is generated in response to a user action.

In one or more embodiments, the aerosol-generating device may allow the user to select whether a generic puff sound or voice message for a user is generated in response to a user action.

The sound generator may be used with any suitable aerosol-generating device. The sound generator may be disposed within, or at least partially within, a body of the aerosol-generating device. The body of the aerosol-generating device may include one or more passages to allow sound from the sound generator to pass to an exterior of the aerosol-generating device.

The aerosol-generating device may be a smoking material heating device. In addition to the MEMS sound generator, the aerosol-generating device may include one or more of a housing, a controller, an aerosolizer, a substrate sensor, an actuator, a battery, a puff sensor, an aerosol-generating substrate receivable in a cavity defined by the housing, and a thermal break element disposed between the cavity and the controller.

The aerosol-generating device may include an aerosolizer to generate aerosol from an aerosol-generating substrate. The controller may be operatively coupled to the aerosolizer to deliver power for aerosolizing the aerosol-generating substrate from a power source, such as a battery. The aerosol-generating substrate may be removably coupled to the aerosolizer or housing of the aerosol-generating device. The aerosol-generating substrate may be at least partially inserted, received, or disposed in the housing of the aerosol-generating device.

In some embodiments, the aerosolizer may be a heating blade that heats a smoking material substrate to generate aerosol from the smoking material. The aerosol-generating substrate may be contained in a substrate housing. The substrate may be described as, or as a content of, a heat stick. The aerosolizer may be coupled to the consumable device to aerosolize the heat stick or the heat stick contents. In some embodiments, the heating blade may be inserted into the heat stick to heat the aerosol-generating substrate. The heat provided by the heating blade to the heat stick may not burn the smoking material. The smoking material may include tobacco.

In some embodiments, the aerosolizer may include a heater, a heater coil, a chemical heat source such as a carbon heat source, or any suitable means that heats a liquid substrate to generate aerosol from a liquid substrate. The aerosolizer may receive electrical energy or power to release or generate aerosol from the liquid substrate. In some embodiments, the aerosolizer may be a heater that varies in temperature depending on the electrical energy received. For example, the heater may rise in temperature in response to a higher voltage received. The aerosolizer may be disposed adjacent to the aerosol-generating substrate. For example, the aerosolizer may be coupled adjacent to the liquid substrate.

In some embodiments, the aerosolizer may be compatible for use with an aerosol-generating substrate having a nicotine source and a lactic acid source. The nicotine source may include a sorption element, such as a PTFE wick with nicotine adsorbed thereon, which may be inserted into a chamber forming a first compartment. The lactic acid source may include a sorption element, such as a PTFE wick, with lactic acid adsorbed thereon, which may be inserted into a chamber forming a second compartment. The aerosolizer may include a heater to heat both the nicotine source and the lactic acid source. Then, the nicotine vapor may react with the lactic acid vapor in the gas phase to form an aerosol.

In some embodiments, the aerosolizer may be compatible for use with an aerosol-generating substrate having a capsule that contains nicotine particles and disposed in a cavity. During a user's inhalation, the air flow may rotate the capsule. The rotation may suspend and aerosolize the nicotine particles.

The actuator may be operatively coupled to the controller. The actuator may include a button or other type of switch. The engagement of the actuator may initiate various functionality of the aerosol-generating substrate. In some embodiments, the sound generator produces the sound information for a user in response to engagement of the actuator. In some embodiments, the aerosolizer may be activated in response to engagement of the actuator.

The puff sensor may be operatively coupled to the controller. The puff sensor may be positioned within an airflow channel in the aerosol-generating device to detect when a user inhales, or puffs, on the device. The puff may be detected by the controller using the puff sensor. Non-limiting types of puff sensors may include one or more of a vibrating membrane, a piezoelectric sensor, a mesh-like membrane, a pressure sensor (for example, a capacitive pressure sensor), and an airflow switch.

One or more of the controllers described herein may include a processor, such as a central processing unit (CPU), computer, logic array, or other device capable of directing data coming into or out of the aerosol-generating device. In some embodiments, the controller includes one or more computing devices having memory, processing, and communication hardware. The functions of the controller may be performed by hardware or as computer instructions on a non-transient computer readable storage medium.

The processor of the controller may include any one or more of a microprocessor, a controller, a microcontroller, a digital signal processor (DSP), an application specific integrated circuit (ASIC), a field-programmable gate array (FPGA), or equivalent discrete or integrated logic circuitry. In some examples, the processor may include multiple components, such as any combination of one or more microprocessors, one or more controllers, one or more DSPs, one or more ASICs, or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors or memory. Program code or logic described herein may be applied to input data/information to perform functionality described herein and generate desired output data/information. The output data/information may be applied as an input to one or more other devices or methods as described herein or as would be applied in a known fashion. In view of the above, it will be readily apparent that the controller functionality as described herein may be implemented in any manner known to one skilled in the art.

The controller may be operatively coupled to the sound generator. The controller may be configured to initiate the sound generator into producing a sound. The controller may include one or more of a processor, a memory, a communication interface, and a circuit board. The circuit board may be coupled to one or more of the processor, the memory, and the communication interface. The processor may be operatively coupled to the memory, the sound generator, the communication interface, the aerosolizer, and the substrate sensor.

The controller may execute a sub-routine to collect an address in memory of a puff sound. A sub-routine may fetch sound puff data at the address. A sub-routine may send puff sound data to the sound generator for producing the sound.

The memory may store one or more sounds at one or more addresses as sound data and may store other data. The memory may store a plurality of sounds. The sound data may be digital data used to produce high-fidelity sound with the sound generator. The sound data may be stored to provide sufficient frequency and amplitude content to produce a high-fidelity sound. Preferably, when uncompressed, the frequency content may contain at least about 40,000 points per second of sound. The amplitude content may be represented by multiple bits per point. For example, the amplitude content may contain about 16 bits per point. The raw digitization of high-fidelity sound may have a sampling rate of about 80 kilobytes per second (KB/s) for uncompressed sound data.

In another manner of characterization, high-fidelity sound may be described as sound containing all frequencies between 20 Hz to 20 kHz represented as 16-bit samples at a 44.1 kHz sampling rate. This high-fidelity sound may be represented by 88.2 KB/s of uncompressed sound data or 264.2 kilobytes for a 3 second puff sound.

In some embodiments, MP3 compression or any other suitable compression technique may be used to reduce the size of the sound data stored in memory compared to uncompressed sound. MP3 compression may reduce high-fidelity sound data by about 90%, or one tenth of the original sampling rate. For example, uncompressed sound data at a sampling rate of about 80 KB/s may correspond to a rate as low as about 8 KB/s when converted to compressed sound data. Any suitable compression quality may be used that still produces high-quality sound.

The memory may have enough space to store multiple puff sounds, which may be described as a library of sounds. Preferably, the memory stores two or more sounds emulating the sound of a conventional use of a smoking material. Each puff sound may have a duration ranging between about 1 second to about 5 seconds. In some embodiments, the puff sound is about 1, about 2, about 3, about 4, about 5, or more seconds. Preferably, the puff sound is about 3 seconds. The memory may store any number of puff sounds according to the space available in the memory. In some embodiments, the memory stores 1, 2, 3, 4, 5, or more puff sounds. Preferably, the memory stores 4 puff sounds. In some embodiments, each puff sound may be stored as about 48 kilobytes of compressed sound data. In some embodiments, a plurality of puff sounds may be stored as about 192 kilobytes of compressed sound data.

Additionally, or alternatively, the memory may have enough space to store information for the user. Information for the user may be instructions for using or maintaining the aerosol-generating device. Each of the instructions may have a duration ranging between about 1 second and about 120 seconds. The memory may store one or more instructions according to the space available in the memory. Preferably, an instruction has a duration of about 1 minute.

The memory may be small enough to fit into a body of the aerosol-generating substrate while storing one or more sounds. The memory may have sufficient space to store at least about 4 different puff sounds and about 1 minute of information. The memory may fit into an area of less than or equal to about 5 mm×about 5 mm. Preferably, the memory fits into a volume of less than about 3 mm×about 2 mm.

The substrate sensor may be disposed adjacent to the cavity. The substrate sensor may be utilized by the controller to automatically detect a type of aerosol-generating substrate received in the cavity.

The aerosol-generating device may operate in one or more modes. Non-limiting examples of modes may include a puff sound mode, an information mode, a substrate detection mode, a data download mode, and a configuration mode.

Each of the modes may be enabled or disabled individually or in combination with one or more other modes. A user action may be used to enable or disable one or more of the different modes or to initiate functions in the one or more modes. For example, the user may engage the actuator in various manners to select various modes or to initiate various functions.

A user action may be an action detectable by the controller. In some embodiments, a user action may include one or more puffs by the user. In some embodiments, the user action may include coupling the aerosol-generating substrate to the aerosolizer. In some embodiments, the user action may include engaging the actuator.

The same or different user actions may be used to initiate various functionality of each mode. For example, in a puff sound mode, sound may be initiated in response to a user puff, whereas in an information mode, sound may be initiated by an engagement of the actuator.

One of the puff sound modes may be a specific puff sound mode. The controller may detect one or more user puffs. In response to detecting the one or more puffs, sound data representing the specific puff sound may be read from the memory. The sound generator may be initiated by the controller into producing the specific puff sound based on the sound data.

One of the puff sound modes may be a generic puff sound mode. The generic sound produced may be white noise or other noise to mask other sounds. In response to detecting one or more puffs, sound data representing the generic sound may be read from the memory. The sound generator may be initiated by the controller into producing the sound emulating the generic sound, such as white noise, based on the sound data.

One of the information modes may be an instruction mode. The controller may read sound data representing an instruction from the memory. The sound generator may be initiated by the controller into producing the sound based on the sound data. In some embodiments, in response to the aerosol-generating device being powered on, the controller may initiate production of sound representing the instruction. In some embodiments, in response to one or more user engagements of the actuator (for example, four consecutive presses), the controller may initiate production of sound representing the instruction.

One of the information modes may be an error message mode to provide an error status of the aerosol-generating device. The controller may supervise a user action and detect an error affecting the aerosol-generating device. In response to detecting the error, the controller may read sound data indicating an error from the memory. The sound generator may be initiated by the controller into producing the sound representing an error message based on the sound data. The error message may be provided as a voice message.

One of the information modes may be an operational message mode to provide the user with the aerosol-generating device status. A user message may be provided as one or more beeps, one or more tones, or preferably, a voice message. The controller may detect a user action. In response to the user action, the controller may read sound data associated with the user action from the memory. In some embodiments, in response to a quick engagement of the actuator, the controller may initiate production of a voice message indicating a battery test (for example, "Button pressed, starting battery test, device will not start"), whereas a more prolonged engagement of the actuator may initiate aerosolization and a different voice message (for example, "The device is starting, you can start using it in 30 seconds"). In some embodiments, device status messages to the user may include an indication of puffs left, an indication of a user interaction with the device, and an indication of a function of the device.

One of the modes may be a substrate detection mode. The controller may determine a type of aerosol-generating substrate automatically or after a user action. In some embodiments, in response to the aerosol-generating substrate being coupled to the aerosolizer, the controller determines the type of substrate automatically using the substrate sensor. In response to detecting one or more puffs, the controller may select the specific puffing sound stored in memory that matches, or is associated with, the type of substrate detected.

One of the modes may be a substrate selection mode. The controller may receive information representing the type of aerosol-generating substrate. The substrate type information may be received using the communication interface and may be provided by the user interface device.

One of the modes may be a data download mode. The controller may use the communication interface to receive data, such as sound data to be stored in the memory, which may be provided by the user interface device.

One of the modes may be a configuration mode. The controller may receive a configuration using the communication interface from, for example, a user interface device. In some embodiments, the configuration may define one or more of a type of aerosol-generating substrate, a specific puff sound mode, a generic puff sound mode, an instruction mode, an error message mode, a status message mode, a substrate detection mode, a substrate selection mode, a data download mode, a configuration mode, a volume level, and an audio quality level (for example, based on bitrate and compression level). The configuration mode may be activated, for example, by a pattern of engagement of the actuator or other suitable user input detectable by the controller.

The sound generated that emulates a conventional use of a smoking material or white noise may be modulated based on a user's puff. The user's puff may be characterized by a puff profile. The puff profile may be determined based on one or more measured puffs from the user using the puff sensor. The rate or duration of the puff or puffs may be represented by the puff profile. The puff profile may be used to change a characteristic of the sound, such as frequency or intensity. For example, a higher puff rate, or higher inhalation rate, may be used to increase intensity (for example, the volume) of the sound generated. The change in the sound may emulate the change in conventional uses of smoking material.

The puff sensor may be integral with the aerosolizer. The aerosolizer may have a characteristic measurable by the controller that indicates a characteristic of the user's puff. The measurable characteristic of the aerosolizer may be used to determine the puff profile. In some embodiments, the aerosolizer (for example, in the form of a heat blade) may change a resistance characteristic when the user puffs due to a temperature drop of the aerosol-generating substrate and the aerosolizer. The higher rate of puff may decrease the temperature and the resistance of the aerosolizer. The decreased resistance may result in a higher current flowing through the aerosolizer. The current characteristic may be measured to represent a puff profile.

The communication interface may be used to communicate to a user interface device. Any suitable communication interface may be used to communicate to the user interface device. The communication interface may be wireless, wired, or both. An example of a wireless interface utilizes Bluetooth, such as Bluetooth Low Energy (BLE). An example of a wired interface utilizes a universal serial bus (USB). In some embodiments, the communication interface may be disposed on the same silicon chip or integrated circuit as the processor.

The aerosol-generating device may be used without the user interface device. However, the user interface device may enable various functionalities and provide a user-friendly manner of configuring the aerosol-generating device.

The user interface device may be any suitable device to accept a user selection and communicate with the aerosol-generating device. The user interface device may communicate a configuration to the aerosol-generating device. In some embodiments, the user interface device may be a smartphone or tablet with an application to facilitate communication with the aerosol-generating device.

The user interface device may include a communication interface, a display, and a controller. The communication interface may communicate with the communication interface of the aerosol-generating device. The display may include a user interface engageable by a user to configure the aerosol-generating device, such as a touch screen, to accept user selections. The display may present one or more graphical elements to configure the aerosol-generating device. The controller may be operably coupled to the display and the communication interface.

The controller may display the one or more graphical elements on the display. The controller may receive the user selection using the one or more graphical elements to configure the aerosol-generating device. The controller may communicate with the aerosol-generating device using the communication interface to configure the aerosol-generating device based on the user selection.

A method of using the MEMS sound generator for an aerosol-generating device may include providing the aerosol-generating device with the MEMS sound generator. The method may further include detecting an action of a user of the aerosol-generating device. The method may also include producing the sound using the MEMS sound generator in response to the action of the user.

A non-transitory computer readable storage medium may include a computer program stored which, when run on programmable electric circuitry, causes the programmable electric circuitry to detect an action of a user of an aerosol-generating device and initiate production of a sound using a MEMS sound generator in response to the action of the user.

A system may include one or more of the aerosol-generating devices and user interface devices described herein. However, the aerosol-generating device may be used without the user interface device.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure. Referring now to the drawings, in which some aspects of the present invention are illustrated.

FIG. 1 is a diagram of a device 10 including a MEMS sound generator 12. The device 10 may be described as an aerosol-generating device. The sound generator 12 may be disposed within a housing 14 of the device 10. The device 10 may include a controller 16. The device 10 may include a memory 18, which may be considered part of the controller 16. The controller 16 may initiate the sound generator 12 into producing sound, such as high-fidelity sound. The controller 16 may initiate the aerosolizer 20 into aerosolizing an aerosol-generating substrate 22 coupled to the aerosolizer. The initiation of the sound and the aerosolizing may be associated. For example, sound may be generated by the sound generator 12 while the aerosol is generated in a concurrent, or at least overlapping, manner. As shown, the aerosol-generating substrate 22 may be removably coupled to the aerosolizer 20. The aerosol-generating substrate 22 may be at least partially received in the housing 14 of the device 10.

The device 10 may include an actuator 24. The actuator 24 may be a button switch. The actuator 24 may be engaged (for example, a button switch may be depressed by a user's finger) to initiate one or more functions of the device 10. For example, the actuator 24 may initiate one or both of sound production and aerosolizing. The sound production may include information for a user of the device 10.

The device 10 may include a puff sensor 26. The puff sensor 26 may detect a user puff on the device 10. Upon detecting a puff, the controller 16 may initiate one or both of sound production and aerosolizing. The sound production may include a puff sound, which may be specific to the substrate 22 or generic (for example, white noise).

A power source (not shown) may be included in the device 10. However, external power sources are also contemplated. The power source may provide power to the aerosolizer 20 for the process of aerosolization.

Figure 2:
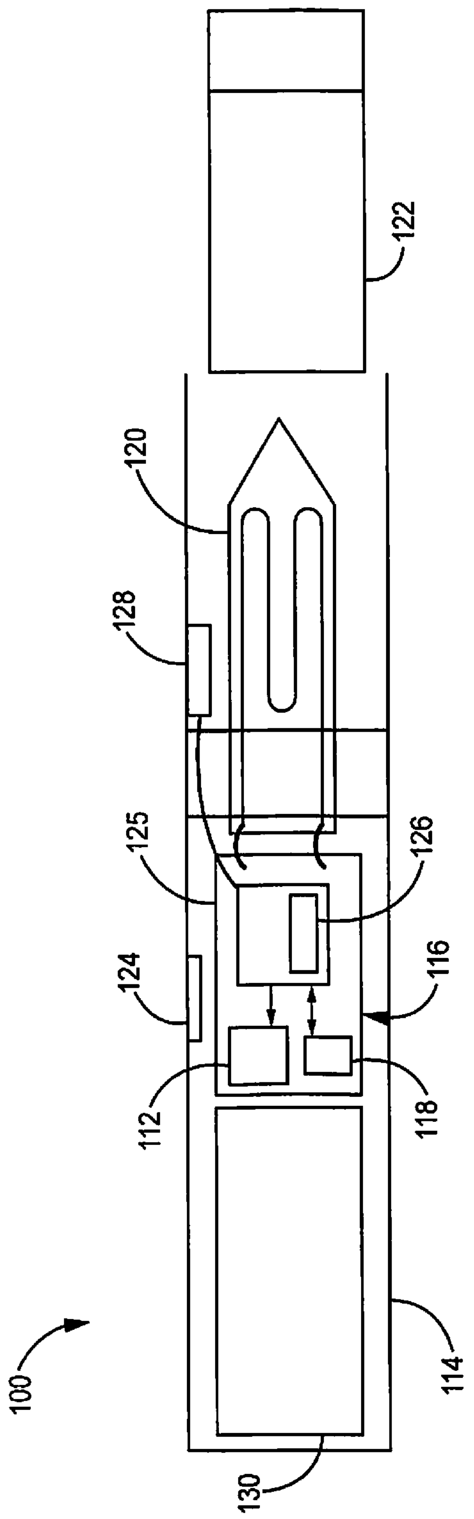

FIG. 2 is a diagram of an aerosol-generating device 100 including a MEMS sound generator 112 used with an aerosol-generating substrate 122 in the form of a heat stick. The heat stick may contain a smoking material that may be heated but not burned to generate aerosol. The device 100 includes an aerosolizer 120 in the form of a heating blade to aerosolize the substrate 122. As shown, the substrate 122 may be removably coupled to the aerosolizer 120.

The device 100 may include a housing 114, a controller 116, a memory 118 to store one or more sounds, an actuator 124, a processor 125, a communication interface 126, a substrate sensor 128, and a power source 130. The communication interface 126 may be disposed on the same silicon chip or integrated circuit as the processor 125. The power source 130 may be a battery.

The substrate sensor 128 may be operatively coupled to the controller 116 to provide an indication of the type of substrate 122 that may be coupled to the aerosolizer 120. The sensor 128 may read an identifier, such as a barcode or color, coupled to the substrate 122.

The communication interface 126 may receive an indication of the type of substrate 122 that may be coupled to the aerosolizer 120.

In addition to aerosolizing, the aerosolizer 120 may be used to measure one or more characteristics of a user's puff, which may be described as a puff profile. For example, the processor 125 of the controller 116 may be used to measure a resistance change in the aerosolizer 120, which may correspond to an inhalation rate as the user puffs. The processor 125 of the controller 116 may be used to modulate the sound generated by the sound generator 112, for example in frequency content or intensity, based on the puff profile. Additionally, or alternatively, an independent puff sensor (not shown) may be included in the device 100.

Figure 3:
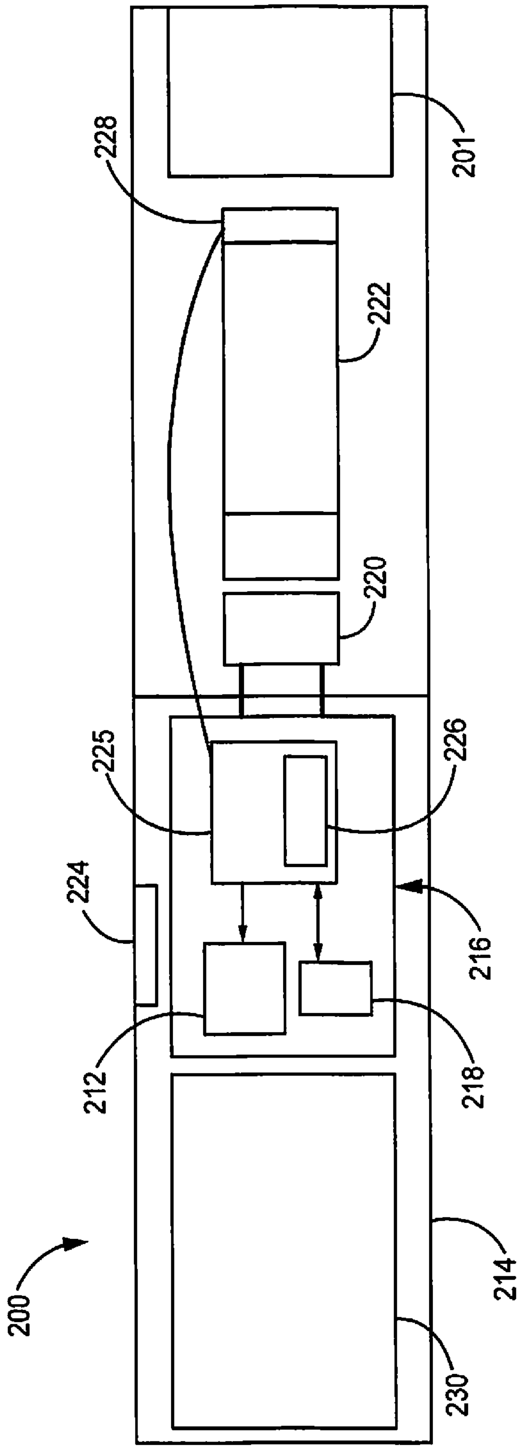

FIG. 3 is a diagram of an aerosol-generating device 200 including a MEMS sound generator 212 used with an aerosol-generating substrate 222 in the form of a liquid substrate (for example, contained in a cartridge 221). The substrate 222 may evaporate upon heating to generate aerosol. The device 100 includes an aerosolizer 220 in the form of a heater adjacent to the substrate 222. As shown, the cartridge 221 containing the substrate 222 may be removably coupled to the aerosolizer 220.

The device 200 may include a mouthpiece 201, a housing 214, a controller 216, a memory 218 to store one or more sounds, an actuator 224, a processor 225, a communication interface 126, and a power source 230. The communication interface 226 may be disposed on the same silicon chip or integrated circuit as the processor 225. The power source 230 may be a battery.

The controller 216 may communicate with a substrate identifier 228 coupled to the substrate 222 (for example, coupled to the cartridge). For example, the substrate identifier 228 may be a wireless tag (for example, an RFID tag). The controller 216 may receive, or read, an identifier from the substrate identifier 228 to provide an indication of the type of substrate 222 that may be coupled to the aerosolizer 220. The communication interface 226 may receive an indication of the type of substrate 222 that may be coupled to the aerosolizer 220, for example, from the substrate identifier 228 or a user interface device.

Figure 4:
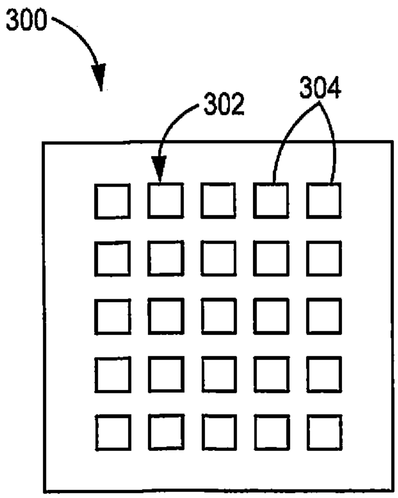

FIG. 4 is a diagram of a MEMS sound generator 300. The sound generator 300 may include an array 302 of pressure-generating drivers 304. Each driver 304 may generate one or more frequencies. Each driver 304 in the array 302 may produce a different frequency. The sound generator 300 may receive a digital signal or data as input. The sound generator 300 may utilize digital sound reconstruction (DSR) to provide high-fidelity sound. As illustrated, the array 302 may be square shaped and have an equal number of rows and columns. However, any suitable shape and number of rows and columns may be used to provide the high-fidelity sound.

Figure 5:
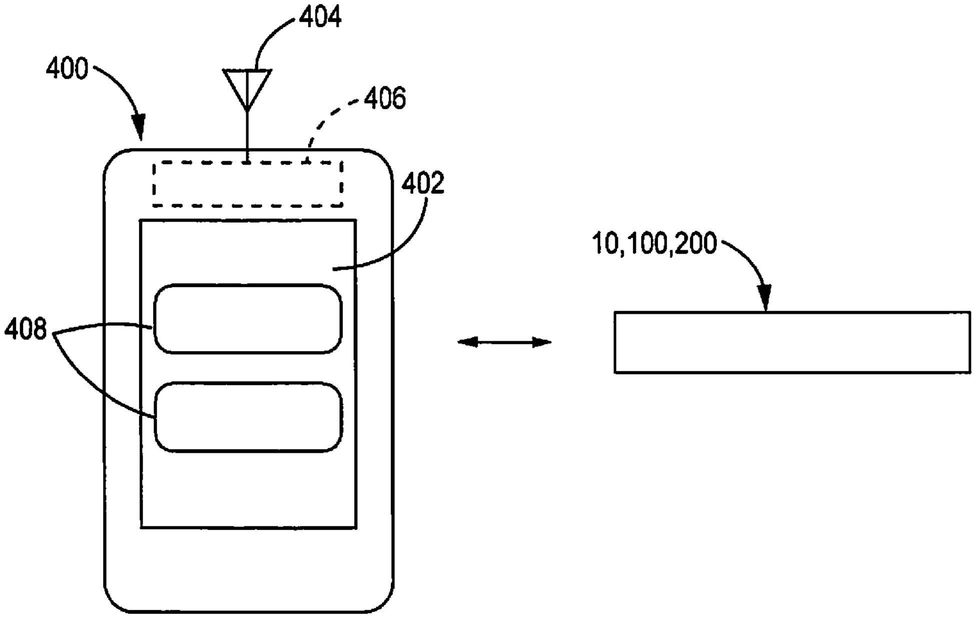

FIG. 5 is a diagram of a user interface device 400 in communication with an aerosol-generating device 10, 100, 200. The device 400 may include a display 402 with a user interface to display one or more graphical elements 408. The user interface may include a touch screen.

The device 400 may include a communication interface 404 operatively coupled to a controller 406 to communicate with the aerosol-generating device 10, 100, 200. As illustrated, the communication interface 404 may be wireless. However, a wired interface is also contemplated. The controller 406 may communicate with the aerosol-generating device 10, 100, 200 using the communication interface 404 to, for example, provide a configuration or sound data to the aerosol-generating device.

Figure 6:
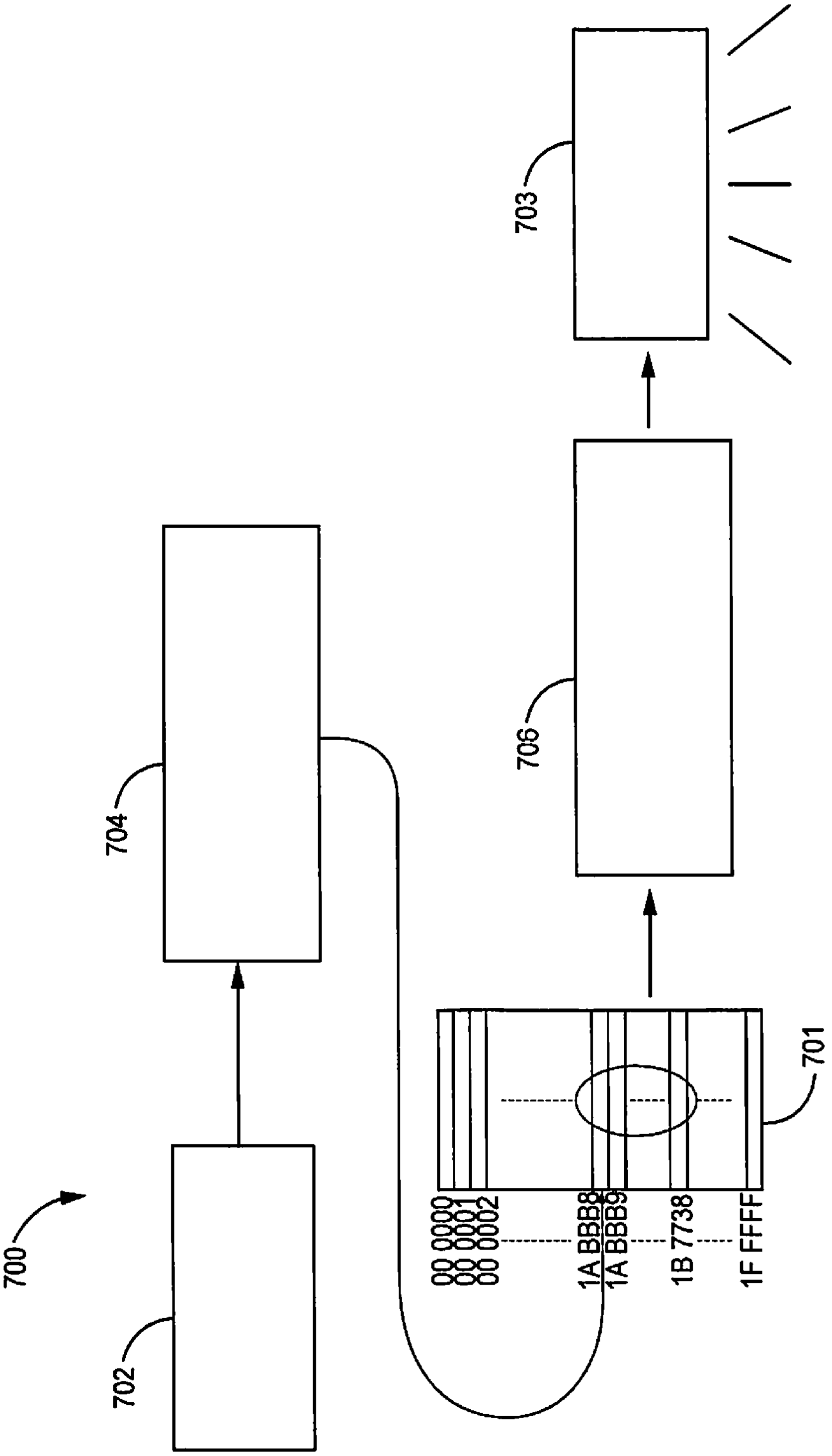

FIG. 6 is a flowchart of a method 700 to detect a puff and produce a puff sound. In process 702, the puff may be detected, which may be carried out by hardware (for example, a puff sensor or heating blade) and a controller subroutine. The controller may include a microcontroller. In process 704, once a puff is detected, a puff sound address may be identified and the puff sound data at the puff sound address may be retrieved from memory 701, which may be carried out in a controller subroutine. In process 706, the audio data may be sent to the sound generator 703 to produce the puff sound. The sound generator may be a microspeaker.

The specific embodiments described above are intended to illustrate the invention. However, other embodiments may be made without departing from the spirit and scope of the invention as defined in the claims, and it is to be understood that the specific embodiments described above are not intended to be limiting.

All scientific and technical terms used herein have meanings commonly used in the art unless otherwise specified. The definitions provided herein are to facilitate understanding of certain terms used frequently herein.

The term "coupled" refers to elements being attached to each other either directly (in direct contact with each other) or indirectly (having one or more elements between and attaching the two elements).

The term "operatively coupled" refers to elements being associated in a manner capable of performing a function involving the elements.

As used herein, the singular forms "a," "an," and "the" encompass embodiments having plural referents, unless the content clearly dictates otherwise.

As used herein, "or" is generally employed in its sense including "and" unless the content clearly dictates otherwise. The term "or" means one or all the listed elements or a combination of any two or more of the listed elements.

As used herein, "have," "having," "include," "including," "comprise," "comprising" or the like are used in their open-ended sense, and generally mean "including, but not limited to". It will be understood that "consisting essentially of," "consisting of," and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

The invention claimed is:

1. An aerosol-generating device comprising:

an aerosolizer comprising a heater to generate aerosol from an aerosol-generating substrate in a form of a heat stick comprising tobacco, the aerosol-generating substrate comprising an identifier to indicate a type of the aerosol-generating substrate;

a MEMS sound generator comprising an array of pressure-generating drivers configured to use digital sound reconstruction (DSR) to use a summation of discrete pulses to produce sound;

a controller operatively coupled to initiate the MEMS sound generator into producing sound, and the controller comprising memory, the memory storing a plurality of high-fidelity sounds; and a substrate sensor operatively coupled to the controller to detect, using the identifier, the type of the aerosol-generating substrate.

2. The device according to claim 1, wherein the array of pressure-generating drivers produces a plurality of different frequencies.

3. The device according to claim 1, further comprising an actuator operatively coupled to the controller and wherein the MEMS sound generator produces high-fidelity sound information in response to engagement of the actuator.

4. The device according to claim 1, wherein to initiate the MEMS sound generator into producing high-fidelity sound comprises producing high-fidelity sound in response to a user puff.

5. The device according to claim 4, wherein to initiate the MEMS sound generator into producing high-fidelity sound comprises modulating, in one or more of intensity and frequency, in response to the user puff.

6. The device according to claim 4, further comprising a puff sensor operatively coupled to the controller to measure the user puff.

7. The device according to claim 4, wherein the controller is further configured to measure a characteristic of the aerosolizer to measure the user puff.

8. The device according to claim 1, wherein the controller is configured to change a characteristic of the high-fidelity sound based on a puff rate or an inhalation rate determined from measured user puffs.

9. The device according to claim 1, wherein the MEMS sound generator uses DSR to produce high-fidelity sound, wherein sound data representative of high-fidelity sound comprises at least 40,000 points per second of sound when uncompressed.

10. The aerosol-generating device according to claim 1, wherein the controller is configured to determine, using the substrate sensor, the type of the aerosol-generating substrate and to select a sound of the plurality of high-fidelity sounds associated with the determined type of the aerosol-generating substrate.

11. A method for use with an aerosol-generating device, the method comprising:

detecting an action of a user using the aerosol-generating device according to claim 1; and producing a high-fidelity sound using the MEMS sound generator in response to the action of the user, wherein the MEMS sound generator comprises an array of pressure-generating drivers using digital sound reconstruction (DSR) to use a summation of discrete pulses to produce the high-fidelity sound.

12. The method according to claim 11, wherein producing high-fidelity sound comprises producing high-fidelity sound that emulates the sound of a conventional use of a smoking material.

13. The method according to claim 12, wherein producing a high-fidelity sound comprises producing high-fidelity sound that emulates the sound of burning kretek.

14. The method according to claim 11, wherein producing a high-fidelity sound comprises producing high-fidelity sound that emulates a white noise.

15. The method according to claim 11, wherein producing a high-fidelity sound comprises producing high-fidelity sound that comprises information for a user.

16. The method according to claim 15, wherein information in the produced a high-fidelity sound comprises a voice message.

17. The method according to claim 15, wherein information in the produced a high-fidelity sound provides an instruction to use or maintain the aerosol-generating device, a status of the aerosol-generating device, or both.

18. A system comprising:

the aerosol-generating device according to claim 1; and a user interface device comprising:

a communication interface to communicate with the aerosol-generating device;

a display comprising a user interface to present one or more graphical elements to configure the aerosol-generating device; and a controller operably coupled to the display and communication interface, the controller configured to:

display the one or more graphical elements on the display;

allow a user selection using the one or more graphical elements via the user interface to configure the aerosol-generating device; and communicate with the aerosol-generating device using the communication interface to configure the aerosol-generating device based on the user selection.

19. The system according to claim 18, wherein the controller of the user interface device is configured to communicate a configuration to the aerosol-generating device defining one or more of: a type of aerosol-generating substrate, a specific puff sound mode, a generic puff sound mode, an instruction mode, an error message mode, an operational message mode, a substrate detection mode, a substrate selection mode, a data download mode, a configuration mode, a volume level, and an audio quality level.

20. The method of claim 11, wherein producing the high-fidelity sound using the MEMS sound generator comprises changing a characteristic of the high-fidelity sound based on a puff rate or an inhalation rate determined from measured user puffs.

* * * * *